United States Patent [19]

Kuroki et al.

[11] Patent Number: 5,476,587
[45] Date of Patent: Dec. 19, 1995

[54] LEUKOCYTE-SEPARATING FILTER AND LEUKOCYTES REMOVER

[75] Inventors: Hitoshi Kuroki; Shoji Ochiai, both of Fujinomiya, Japan

[73] Assignee: Terumo Kabushiki Kaisha, Tokyo, Japan

[21] Appl. No.: 193,505

[22] Filed: Feb. 8, 1994

[30]  Foreign Application Priority Data

Jun. 27, 1993 [JP] Japan ................................ 5-179917

[51] Int. Cl.⁶ ............................ B01D 39/00; B01D 29/00
[52] U.S. Cl. ..................... 210/496; 210/510.1; 422/101
[58] Field of Search .................................... 210/496, 504, 210/505, 506, 507, 508, 510.1, 503; 422/101; 428/36.5, 220, 428, 304.4, 314.4, 314.8, 315.9; 428/304.4, 314.4, 314.8, 315.9

[56] References Cited

U.S. PATENT DOCUMENTS

| | | | |
|---|---|---|---|
| 4,701,267 | 10/1987 | Watanabe et al. | 210/505 |
| 4,880,548 | 11/1989 | Pall et al. | 210/508 |
| 4,936,998 | 6/1990 | Nishimura et al. | 210/508 |
| 4,985,153 | 1/1991 | Kuroda et al. | 210/496 |
| 5,234,593 | 8/1993 | Kuroki et al. | 210/510.1 |

FOREIGN PATENT DOCUMENTS

| | | |
|---|---|---|
| 0408462 | 1/1991 | European Pat. Off. . |
| 0419346 | 3/1991 | European Pat. Off. . |
| 47-46455 | 11/1972 | Japan . |
| 48-20019 | 6/1973 | Japan . |
| 63-39060 | 9/1986 | Japan . |
| 61-39060 | 9/1986 | Japan . |
| 63-26089 | 5/1988 | Japan . |

OTHER PUBLICATIONS

Patent Abstract of Japan 63 255 070 (Oct., 1988).
Patent Abstract of Japan JP 50 34 337, vol. 17, No. 314, Sep. 1993.

*Primary Examiner*—John Kim
*Attorney, Agent, or Firm*—Burns, Doane, Swecker & Mathis

[57] ABSTRACT

A leukocyte remover includes a housing having a blood inlet, a blood outlet, and a leukocyte-separating filter disposed in the housing such that it partitions the interior of the housing into a blood inlet portion and a blood outlet portion. The leukocyte filter is composed of one or more three-dimensionally reticular, porous members with continuous open pores having a most frequent pore diameter of 1 µm to 5 µm and a ratio of a weight-average pore diameter to a number-average pore diameter in the range of 1.5 to 2.5.

3 Claims, 13 Drawing Sheets

LEUKOCYTE-SEPARATING FILTER AND LEUKOCYTES REMOVER

BACKGROUND OF THE INVENTION

1. Field of the Present Invention

This invention relates to filters for separating leukocytes, leukocyte removers, filters for separating both leukocytes and platelets, and leukocyte/platelet removers, and more particularly to those having excellent capability of capturing leukocytes without suffering from contamination with foreign matters.

2. Prior Art

In recent years, the form of blood transfusion has been changed from conventional whole blood transfusion to blood component transfusion by which only a necessary component is transfused to a patient. The important point of the blood component transfusion is how to increase the purity of respective blood components fractionated.

Blood from donors has conventionally been centrifugally separated into concentrated red cells (CRC), a platelet concentrate (PC), and a platelet-poor plasma (PPP). Blood preparations obtained by the separation of blood are used for blood component transfusion to patients who need red cells or platelets. However, since a large amount of leukocytes are contained in blood preparations, problems may sometimes take place by injecting a large amount of leukocytes into patients by transfusion.

Leukocytes contained in blood preparations must be removed to the possible extent for the purpose of avoiding side effects, namely post-transfusion reactions. To date, a number of improvements have been proposed for this purpose. In some cases, extraction of red cells alone by excluding leukocytes and platelets is also required. Used for these purposes are a method using a capturing member, a gravitational centrifugal separation method utilizing the difference in specific gravity between blood cells, a method utilizing the viscidity or adhesion of leukocytes, etc.

Among them, the method using a capturing member is widely used because of good efficiency in removing leukocytes or leukocytes and platelets, easiness of handling, etc. Capture members often used are fibers having extremely small diameters such as natural fibers, synthetic fibers, etc. packed into a column, or non-woven fabrics formed by secondary-processing them.

The use of such fibers, however, is likely to suffer from detachment of some fibers or outflow of foreign matters during operation. If the fiber packing density is increased for the purpose of sufficiently capturing leukocytes or platelets, trapped blood cells tend to clog pores between the fibers.

On the other hand, there are various proposals to use porous members as the capturing members. For example, Japanese Patent Publication No. 61-39060 discloses the use of a porous member including continuous fine pores with an average pore diameter of 25 μm to 60 μm to capture highly viscous monocytes and granulocytes. Japanese Patent Publication No. 63-26089 discloses a method using a porous member having continuous pores with an average pore diameter of 5 μm to 20 μm to capture leukocytes by utilizing the viscidity of white cells and by filtration with the fine pores of the porous members.

However, in view of the recent demand for more effective removal of leukocytes, the above porous members having relatively large pore diameters do not provide satisfactory leukocyte separation. Leukocyte-separating abilities are elevated by reducing the pore diameter (for example, by reducing the average pore diameter to less than 3 μm or so); however, blood cells trapped are likely to clog the pores of the porous members, taking much time for filtration.

Thus, there have so far been no leukocyte filters, leukocyte/platelet-separating filters, and removers comprising such filters with sufficient performance for the practical purpose, and their improvements are still desired.

OBJECTS AND SUMMARY OF THE INVENTION

It is therefore an object of the present invention to provide a leukocyte-separating filter suffering from no outflow of foreign matters during operation, having a high and stable capability of capturing leukocytes, and capable of efficiently and quickly separating leukocytes from blood or blood preparations.

Another object of the present invention is to provide a leukocyte/platelet-separating filter suffering from no outflow of foreign matters during operation, having a high and stable capability of capturing leukocytes and platelets, and capable of efficiently and quickly separating leukocytes and platelets from blood or blood preparations.

A still another object of the present invention is to provide a leukocyte remover comprising such a leukocyte-separating filter.

A still another object of the present invention is to provide a leukocyte/platelet remover comprising such a leukocyte/platelet-separating filter.

The first leukocyte-separating filter according to the present invention comprises as a major element a three-dimensionally reticular, porous member having a three-dimensionally reticular, continuous texture with continuous open pores having a most frequent pore diameter in the range of 1 μm to 5 μm, and such a dust permeability that permits 200 or less dust particles not smaller than 0.3 μm in the atmosphere to pass through the porous member in a period of time in which 100,000 of the same dust particles flow without a filter (blank value).

The second leukocyte-separating filter according to the present invention comprises a three-dimensionally reticular, porous member with continuous open pores having a most frequent pore diameter in the range of 1 μm to 5 μm and a ratio of a weight-average pore diameter to a number-average pore diameter in the range of 1.5 to 2.5.

The first leukocyte/platelet-separating filter according to the present invention comprises a platelet-adsorbing, three-dimensionally reticular, porous member with continuous open pores having a most frequent pore diameter in the range of 1 μm to 5 μm and a ratio of a weight-average pore diameter to a number-average pore diameter in the range of 1.5 to 2.5.

The second leukocyte/platelet-separating filter according to the present invention comprises a laminate of at least one platelet-nonadsorbing, three-dimensionally reticular, porous member with continuous open pores having a most frequent pore diameter in the range of 1 μm to 5 μm and a ratio of a weight-average pore diameter to a number-average pore diameter in the range of 1.5 to 2.5, and at least one platelet-adsorbing, three-dimensionally reticular, porous member with continuous open pores having a most frequent pore diameter in the range of 1 μm to 5 μm and a ratio of a weight-average pore diameter to a number-average pore diameter in the range of 1.5 to 2.5.

The leukocyte remover according to the present invention comprises a housing having a blood inlet and a blood outlet; and a leukocyte-separating filter disposed in the housing such that it partitions the interior of the housing into a blood inlet portion and a blood outlet portion, the leukocyte-separating filter being composed of a three-dimensionally reticular, porous member with continuous open pores having a most frequent pore diameter in the range of 1 μm to 5 μm and a ratio of a weight-average pore diameter to a number-average pore diameter in the range of 1.5 to 2.5.

The leukocyte/platelet remover according to the present invention comprises a housing having a blood inlet and a blood outlet; and a leukocyte/platelet-separating filter disposed in the housing such that it partitions the interior of the housing into a blood inlet portion and a blood outlet portion, the leukocyte/platelet-separating filter being a laminate of at least one platelet-nonadsorbing, three-dimensionally reticular, porous member with continuous open pores having a most frequent pore diameter in the range of 1 μm to 5 μm and a ratio of a weight-average pore diameter to a number-average pore diameter in the range of 1.5 to 2.5, and at least one platelet-adsorbing, three-dimensionally reticular, porous member with continuous open pores having a most frequent pore diameter in the range of 1 μm to 5 μm and a ratio of a weight-average pore diameter to a number pore diameter in the range of 1.5 to 2.5.

DETAILED DESCRIPTION OF THE PREFERRED EMBODIMENTS OF THE INVENTION

Figure 1:
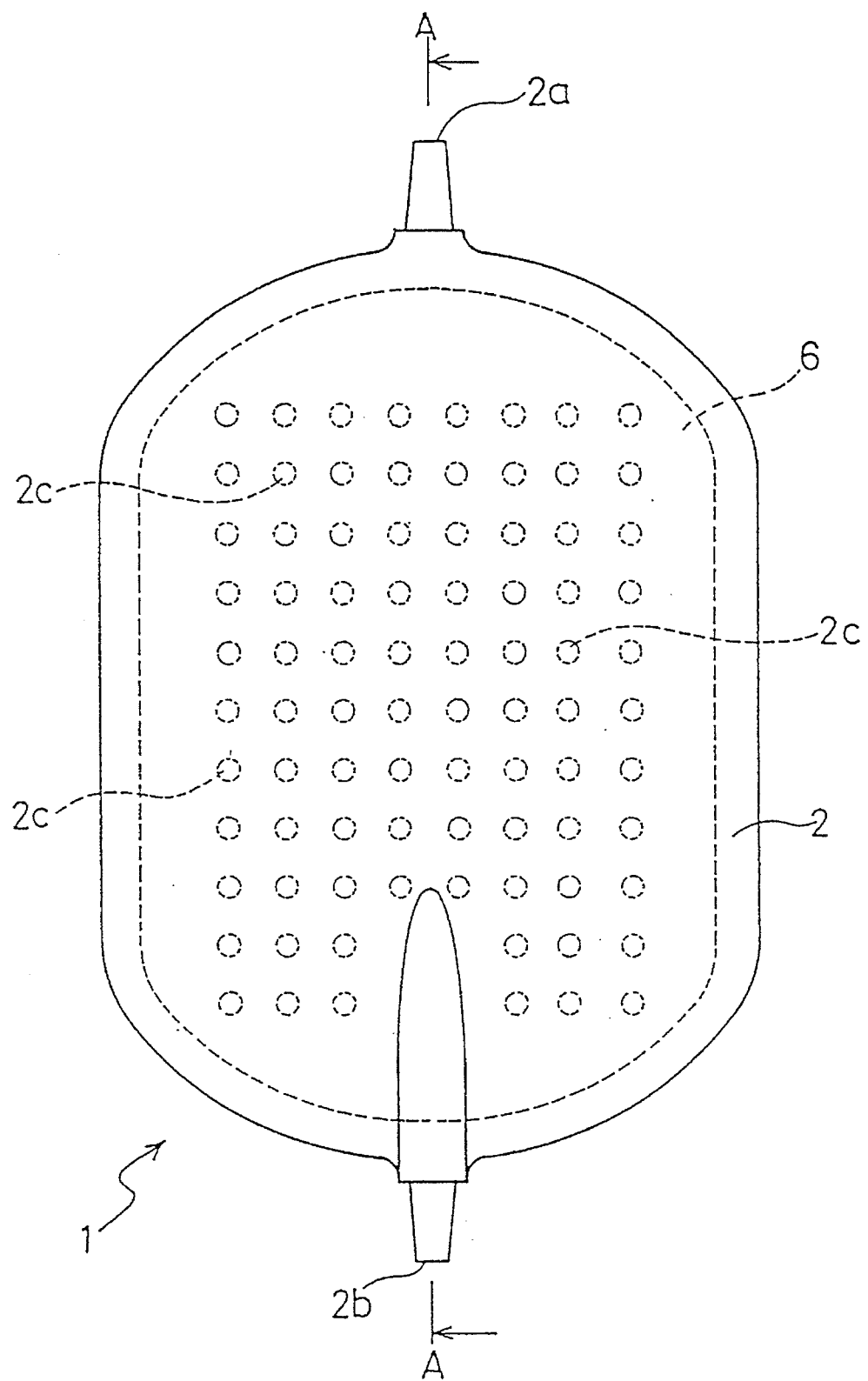
FIG. 1 is front elevational view showing a leukocyte remover including a leukocyte-separating filter according to an embodiment of the present invention.

The present invention will be described below in detail.

[1] Leukocyte-separating filter

A leukocyte-separating filter explained in this Section is one for separating leukocytes alone. A filter for separating both leukocytes and platelets will be explained in Section [2].

The leukocyte-separating filter is composed of a three-dimensionally reticular, porous member having continuous open pores whose most frequent pore diameter is 1 μm to 5 μm. If the most frequent pore diameter is smaller than 1 μm, other blood cells contained in blood or a leukocyte suspension to be treated are also captured during leukocyte removal operation, possibly clogging the filter. On the other hand, if the most frequent pore diameter is larger than 5 μm, the frequency of contact with a leukocyte suspension to be treated is lowered, possibly decreasing the blood cell capturing rate. The more preferable most frequent pore diameter of the leukocyte-separating filter is 2 μm to 4 μm.

The term "most frequent pore diameter" used herein means a pore diameter which the largest number of pores have, and it is defined as a most frequently occurring diameter (peak value) in a distribution of pore diameters. The pore diameter distribution is obtained by cutting a porous member along an arbitrary surface, measuring cross section areas of respective pores distributed throughout the entirety of the cross section surface, calculating diameters of the pores assuming that they are converted into circular pores, and plotting the pore diameters on a graph in which the abscissa indicates pore diameters at 1-μm-intervals and the ordinate indicates the number of pores in every interval (every 1 μm). Thus, the most frequent pore diameter indicates a pore diameter most often shown, regarding all of the pores having variable shapes and diameters as circular cross-sectional pores. In order to ensure a reliability, not less than 2000 pores are preferably measured at random.

By the foregoing definition, the most frequent pore diameter does not necessarily represent the largest diameter among those of the existing pores, but merely means that the number of pores having larger or smaller diameters than the most frequent pore diameter gradually decreases. Therefore, the most frequent pore diameter does not even mean that particles having larger diameters do not pass through the porous member. Although red cells in general have larger diameters than the most frequent pore diameter, living red cells can freely deform and pass through the pores.

The three-dimensionally reticular, porous member with continuous open pores according to the present invention is characterized by having such a dust permeability that permits 200 or less dust particles not smaller than 0.3 μm in the atmosphere to pass through the porous member in a period of time in which 100,000 of the same dust particles flow without a filter (blank value). If the dust permeability exceeds 200, the leukocyte removal rate decreases, and an expected leukocyte removal rate cannot be achieved. A preferable dust permeability is 20 or less.

The dust permeability is measured by the following method. First, a particle counter ("KC-01" produced by RION) is set to operate under the conditions of one-liter evacuation, a flow rate of 500 cc/minute and a measurable minimum particle size of 0.3 μm. After energized, the particle counter is warmed up for at least 30 minutes. With the start button of the particle counter turned on, the period of time required for counting 100,000 dust particles in the air is measured three times, and its average is taken as a blank value.

On the other hand, a porous member cut to a disc having a diameter of 47 mm is set in a filter holder ("SWINEX 47" produced by MILLIPORE). An upper portion of the filter holder equipped with the filter (porous member) is connected to a tip end of a given vinyl chloride resin tube attached to the particle counter. Then, with the start button of the particle counter turned on, the number of dust particles passing through the filter in a period of time equivalent to the blank value is measured. The measurement is repeated three times for every filter, and the average value is taken as the dust permeability.

By replacing the filter holder by a new one, next measurement is done. When the measurement of three filters are completed, the measurement of a blank value is again done. If a new blank value is deviated from the previous one, then measurement is continued with the new blank value.

In another embodiment, the porous member constituting the leukocyte-separating filter is characterized by having an average pore diameter ratio (ratio of a weight-average pore diameter to a number-average pore diameter) of 1.5 to 2.5. If the average pore diameter ratio is less than 1.5, clogging is liable to occur, and filtration takes much time. If it exceeds 2.5, the capturing rate is liable to decrease.

The weight-average pore diameter is a value defined by $\Sigma Ri^2 Ni/\Sigma RiNi$ similarly to the equation of the weight average molecular weight, and the number-average pore diameter is a value defined by $\Sigma RiNi/\Sigma Ni$, where $Ri$ is a pore diameter measured by a mercury infiltration method, and $Ni$ is the number of pores having a diameter $Ri$. The pore diameter $Ri$ is determined by randomly cutting a porous member, measuring cross section areas of respective pores distributed throughout the entirety of the cross section surface, converting the cross sections of the pores to circles, and calculating diameters of the circles. As explained above, the average pore diameter ratio represents a distribution of pore diameters. The larger the value of the average pore diameter ratio, the wider the distribution of pore diameters, meaning that there are many pores having larger diameters than the most frequent pore diameter and many pores having smaller diameters than the most frequent pore diameter.

The porosity of a platelet-nonadsorbing, three-dimensionally reticular, porous member with continuous open pores is preferably 75% to 95% and more preferably 80% to 95%, although it may vary depending on the most frequent pore diameter, etc. When the porosity is 75% or more, leukocytes are removed in a short time. If the porosity is 95% or less, a sufficient strength required for a filter is obtained. The thickness of the porous member is preferably 0.1 mm to 10 mm and more preferably about 0.5 mm to about 3 mm, although it may vary depending on the most frequent pore diameter, porosity and microstructure of the porous member. If the porous member is 0.1 mm or thicker, the filter is strong enough. On the other hand, if it is 10 mm or thinner, the length of filtration path is not excessive, and clogging is unlikely to occur.

The leukocyte-separating filter may be composed either of a single porous member in the form of a flat sheet or of a plurality of such porous members. Preferably, however, a plurality of flat porous members are stacked to provide a laminate. In case where the leukocyte-separating filter is composed of a plurality of porous members, it is preferred to dispose one or more porous members having wider pore diameter distributions (larger average pore diameter ratios) on the upstream side and one or more porous members having narrower pore diameter distributions (smaller average pore diameter ratios) on the downstream side. Placing the porous member having a wider pore diameter distribution on the upstream side provides efficient separation of leukocytes without increasing filtration resistance.

The three-dimensionally reticular, porous member with continuous open pores constituting the leukocyte-separating filter having the above characteristics is made of a platelet-nonadsorbing material. The term "platelet-nonadsorbing" used herein means a characteristic of adsorbing substantially no platelet, and does not necessarily mean absolute non-adsorption of platelets. Preferable materials therefor are ethylene-vinyl alcohol copolymers, polyurethanes of any types including a polyether type, a polyester type and a polycarbonate type (preferably polyurethanes containing polyethers such as polytetramethylene oxide, polypropylene oxide or polyethylene oxide), fluorocarbon polymers (preferably polyvinylidene fluoride), polysulfones, and polyether sulfones. Particularly preferable are polyurethanes.

A preferable method for manufacturing the porous member is a so-called elution method which comprises extruding a fiat sheet made of a resin composition including a polymer such as polyurethane, polyvinylidene fluoride, polysulfone, polyester, polyamide, etc., a good solvent therefor and a pore-creating agent soluble in or swellable with a non-solvent having a compatibility with the good solvent, and then immersing the extruded flat sheet in the non-solvent to cause gelation while eluting out the pore-creating agent, thereby forming a fiat porous sheet or film having "through-pores", pores penetrating from one side to the other of the porous sheet or film. A preferable ratio of the polymer in the resin composition is 5 weight % to 70 weight %. Preferable good solvents are dimethyl formamide, dimethyl sulfoxide, acetone, dioxane, methyl Cellosolve acetate, tetrahydrofuran, ethyl alcohol, methyl alcohol, methyl ethyl ketone, etc. Preferable pore-creating agents are polyvinyl alcohol, polyvinyl pyrrolidone, methyl cellulose, polyether, polysaccharide, polyacrylic acid, etc. A preferable amount of the pore-creating agent added is 5 weight % to 50 weight % based on the composition to provide the porous member with continuous open pores (fine through-pores). This manufacturing method is described in detail in Patent Laid-open No. 3-47131. In the case of polyurethane, it may be coated on another material.

Since the leukocyte-separating filter of the present invention exhibits a high and stable capability of capturing leukocytes, it can efficiently and quickly separate leukocytes from a platelet concentrate (PC), concentrated red cells (CRC) or a whole blood without danger of outflow of foreign matters during operation. Further, the leukocyte-separating filter suffers from little variance in performance.

[2] Filter for Separating Leukocytes and Platelets

A filter for separating leukocytes and platelets (leukocyte/platelet-separating filter) may be either composed of one or more platelet-adsorbing, three-dimensionally reticular, porous member with continuous open pores, or of a laminate of one or more platelet-nonadsorbing, three-dimensionally reticular, porous members with continuous open pores and one or more platelet-adsorbing, three-dimensionally reticular, porous members with continuous open pores. In any case, the porous members have a most frequent pore diameter of 1 μm to 5 μm and an average pore diameter ratio (ratio of a weight-average pore diameter to a number-average pore diameter) of 1.5 to 2.5 in order to have a good leukocyte-separating capability. For the same reason as stated above, the most frequent pore diameter is preferably 2 μm to 4 μm.

The platelet-nonadsorbing, three-dimensionally reticular, porous member with continuous open pores may be the same as explained in [1] above. In contrast, the platelet-adsorbing, three-dimensionally reticular, porous member with continuous open pores may be made either of a platelet-adsorbing material or of a cationic-treated platelet-nonadsorbing or platelet-adsorbing material.

Platelet-adsorbing materials usable in the present invention are polyvinyl acetals (preferably polyvinyl formal), aliphatic polyamides which may be nylon 6, nylon 66, nylon 12, or so-called polyetheramides copolymerized with polyether components such as polytetramethylene oxide, polypropylene oxide and polyethylene oxide, aromatic polyamides (preferably, in particular, polymethaphenylene isophthalic amide or polyparaphenylene terephthalic amide), polyesters (in particular polybutylene terephthalate, polyethylene terephthalate, etc.), polyimides, etc.

The term "cationic treatment" used herein means to adhere or bond a cationic compound to a surface of a filter substrate or to incorporate the cationic compound into the filter substrate. Specifically, there are methods of coating the porous member with a cationic compound, methods of bonding the cationic compound to the filter substrate by grafting copolymerization, etc., and methods of mixing the filter substrate with the cationic compound in the process of fabrication of the porous member. Cationic compounds usable are quaternary ammonium salts, compounds having amino groups or imino groups, etc. For example, in a preferable method for bonding the cationic compound to the filter substrate by graft copolymerization, the filter substrate is subjected to a plasma treatment, and graft-copolymerized with a monomer having a reactive substituent such as glycidyl methacrylate, and then a cationic agent is bonded to the grafted monomer. Cationic treatment contributes to maintaining a positive charge of the filter for a long period of time.

The porous member constituting the leukocyte/platelet-separating filter, either platelet-nonadsorbing or platelet-adsorbing, preferably has a permeability of 200 or less for dust particles of 0.3 μm or larger as in the case of [1] above.

The platelet-adsorbing three-dimensionally reticular, porous member with continuous open pores has a porosity of 75% to 95% and a thickness of 0.1 mm to 10 mm for the reason described in [1] above.

The platelet-adsorbing, three-dimensionally reticular, porous member with continuous open pores may be produced by any method, provided that the porous member has the aforementioned structure. A preferable method is an elution method. In the case of making the porous member of polyvinyl formal, for example, the elution method uses an acetal-forming reaction by which formaldehyde and an acid catalyst acts on an aqueous polyvinyl alcohol solution containing a pore-creating agent selected from amylose-containing polysaccharide such as starch and dextrin, derivatives thereof, acid-proof anionic surfactants, nonionic surfactants, etc. optionally in the presence of an inorganic salt such as sodium sulfate, sodium chloride, ammonium sulfate, ammonium chloride, potassium sulfate, sodium iodide, etc. (Patent Publication Nos. 47-46455 and 48-20019).

With a high and stable capability of capturing leukocytes and platelets, the leukocyte/platelet-separating filter of the present invention can efficiently and quickly separate leukocytes and platelets from concentrated red cells (CRC) and a whole blood, without danger of outflow of foreign matters during operation. It also reduces variance in performance.

[3] Leukocyte Remover

A leukocyte remover equipped with the leukocyte-separating filter according to the present invention will be explained below in detail with reference to FIGS. 1 to 3.

Figure 2:
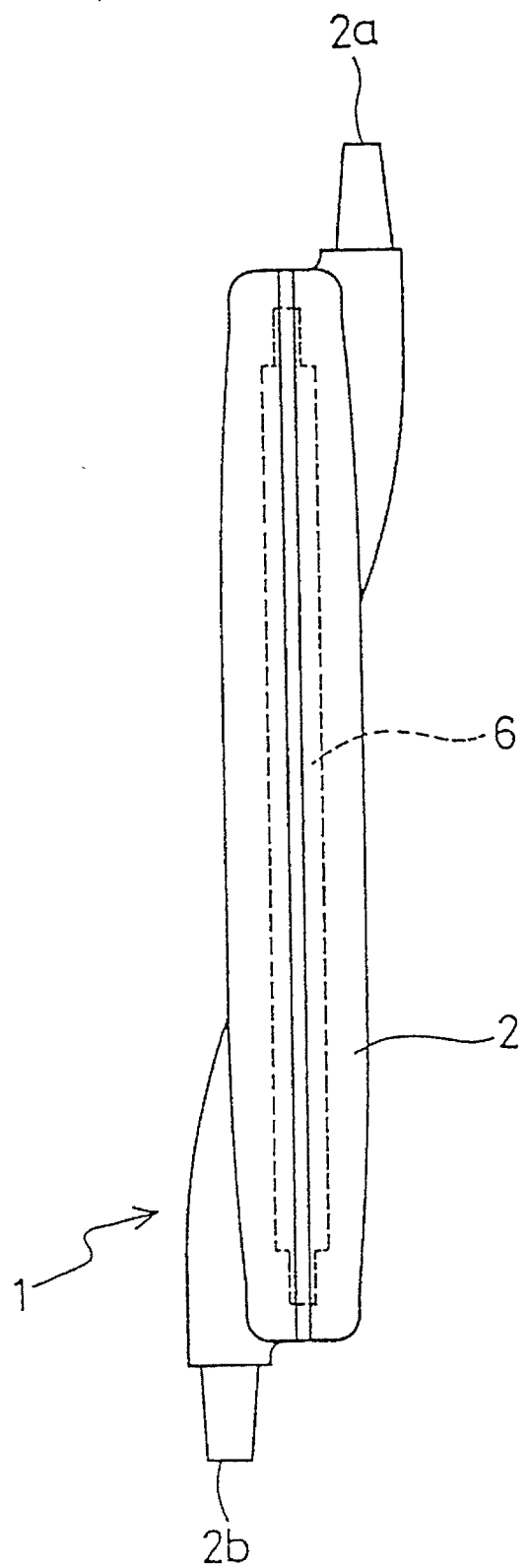
FIG. 2 is a right side elevational view of FIG. 1.
Figure 3:
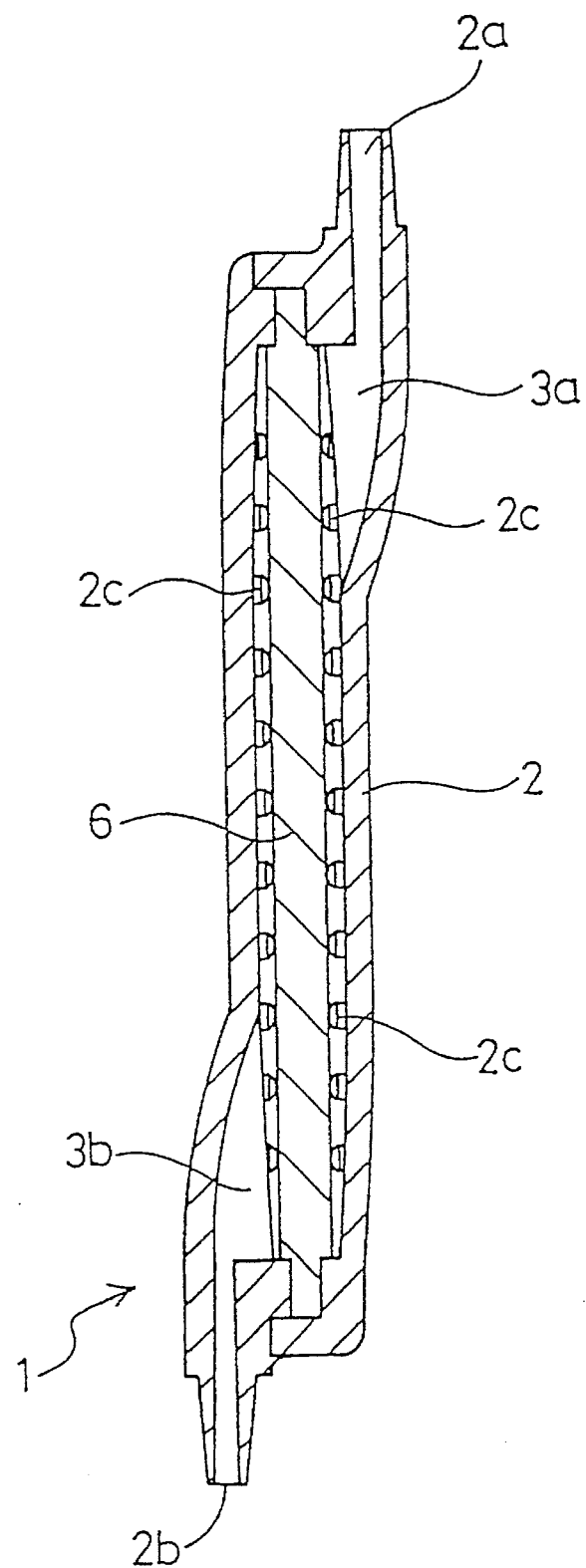
FIG. 3 is a cross-sectional view taken along the A—A line in FIG. 1.

FIG. 1 is a front elevational view of an example of the leukocyte remover with the leukocyte-separating filter according to the present invention, FIG. 2 is a right side elevational view of FIG. 1, and FIG. 3 is a cross-sectional view taken along the A—A line in FIG. 1.

The leukocyte remover 1 with the leukocyte-separating filter 6 according to the present invention is composed of a housing 2 having blood inlet 2a and a blood outlet 2b, and a leukocyte-separating filter 6 constituted by a three-dimensionally reticular, porous member with continuous open pores and disposed in the housing 2 such that it partitions the interior of the housing 2 into a blood inlet portion 3a and a blood outlet portion 3b. As shown in FIG. 3, the filter 6 of the present invention is received in the housing 2 such that blood, etc. introduced into the housing 2 through the blood inlet 2a cannot exit from the blood outlet 2b without passing through the filter 6. A circumferential portion of the filter 6 is water-tightly disposed between inner surfaces of two members of the housing 2. The filter 6, as shown in FIG. 3, is partly clumped by a plurality of projections 2c formed on the inner surface of the two constituent members of the housing 2 to prevent deformation of the filter during operation and storage.

Usable for the housing 2 are various materials such as polycarbonates, acrylic resins, polyethylene terephthalate, polyethylene, polypropylene, polystyrene, polyvinyl chloride resins, acryl-styrene copolymers, acryl-butylene-styrene copolymers, and so on. Particularly preferable are polycarbonates, acrylic resins, polyethylene terephthalate, polyethylene, polypropylene, polystyrene and polyvinyl chloride resins. The inner surface of the housing 2 is preferably treated to have a hydrophilic nature to alleviate adhesion of blood cells thereto. Suitable hydrophilic treatment is coating or bonding of a hydrophilic substance, or a surface treatment such as plasma treatment, corona treatment, etc.

In the leukocyte remover 1 according to one embodiment of the present invention shown in FIG. 3, a pre-filter portion (the right side portion of the filter 6 in FIG. 3) on the upstream side of a main filter portion (the left side portion of the filter 6 in FIG. 3) functions to remove fine particles in the blood (for example, gels, microaggregates, etc.) and huge leukocyte particles among all leukocytes from the blood, before introducing the blood into the main filter portion to prevent clogging of the main filter portion.

A suitable porous member used for the pre-filter portion is a three-dimensionally reticular, porous member with continuous open pores having a most frequent pore diameter of about 2 μm to about 4 μm, an average pore diameter ratio of 2.0 to 2.5, and a thickness of about 0.3 mm to about 1.5 mm. A suitable number of such porous members laminated is 1 to 5. A suitable porous member used for the main filter portion is a three-dimensionally reticular, porous member with continuous open pores having a most frequent pore diameter of about 1 μm to about 3 μm and smaller than that of the pre-filter portion, an average pore diameter ratio of 1.5 to 2.0, and a thickness of about 0.3 mm to about 1.5 min. A suitable number of such porous members laminated is 1 to 5.

In a preferred embodiment, the pre-filter portion may be made by stacking two porous polyurethane films each having a most frequent pore diameter of 2.5 μm to 3.5 μm, an average pore diameter ratio of 2.5, and a thickness of about 0.6 mm and treated by a surfactant, and the main filter portion may be made by stacking four porous polyurethane members each having a most frequent pore diameter of 1.0 μm to 2.0 μm, an average pore diameter ratio of 1.7, and a thickness of about 0.6 mm and treated by a surfactant.

The filter may be a single-layered member in lieu of the laminate stated above. The thinner the filter, the easier it is to make the integral structure uniform, and the easier the fabrication of a filter meeting the desired numerical conditions. Further, taking intended use, sheet areas and other factors into consideration, any appropriate number of sheets may be laminated to make a desired leukocyte remover. The number of porous sheets laminated may appropriately be determined by considering the removal rate, filtration time, likelihood of clogging, etc.

Any surfactant may be used for a hydrophilic treatment, and suitably usable are, for example, glycerol monolaurate, and polyether-type surfactants (for example, Pluronic surfactant). Instead of using a surfactant, the porous member may be hydrophilic-treated (for example, plasma-treated).

Figure 7:
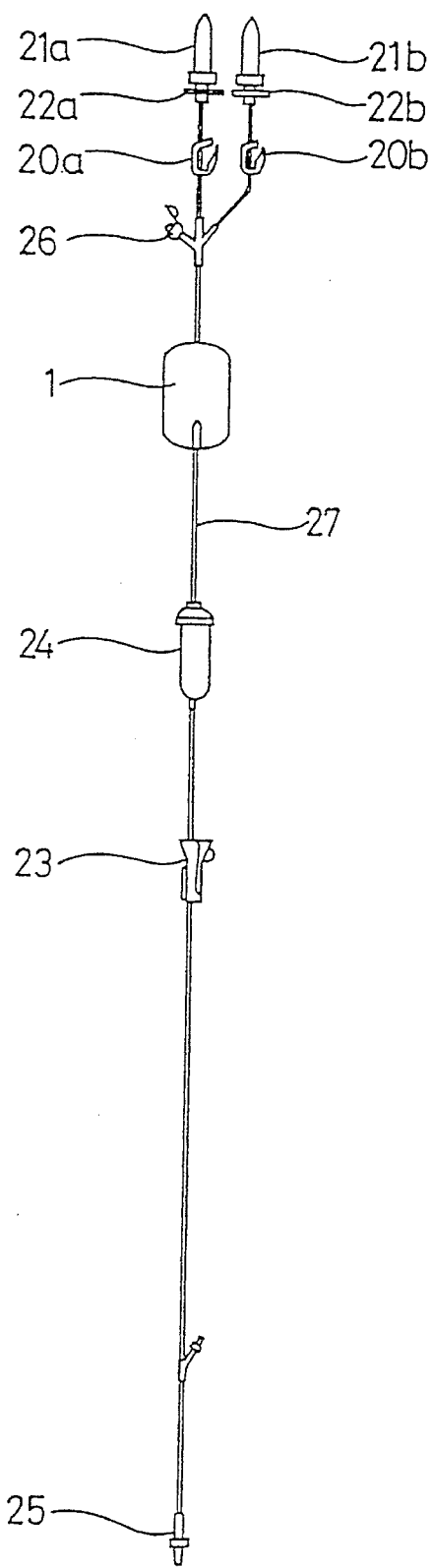
FIG. 7 is a schematic view showing a circuit including the leukocyte-separating filter according to the present invention.

An example of usage of the leukocyte-separating filter 6 of the present invention will be explained below with reference to FIG. 7 showing a circuit for removing leukocytes from a blood preparation such as platelet concentrate which does not contain red cells for component transfusion of platelets to a patient.

The separation of leukocytes with the circuit of FIG. 7 is started by closing clamps 20a, 20b. Protectors 21a, 21b are then removed, and needles 22a, 22b are attached to a bag (not shown) of a blood preparation (specifically, platelet concentrate) and to a rinse bag (not shown). The blood preparation bag and the rinse bag are hung down from an irrigator (not shown).

While maintaining the leukocyte remover 1 upside down, the clamps 20a and a roller clamp 23 are opened for priming the leukocyte remover 1. After the priming of the leukocyte remover 1 is completed, the leukocyte remover 1 is returned to the original posture. After that, by making an instillator 24 upside down, the blood preparation is introduced into the instillator 24. After the blood preparation occupies about a half volume of the instillator 24, the instillator 24 is returned to the original posture. When the blood preparation reaches a tip end of a lock connector 25, the roller clamp 23 is closed.

With a syringe needle attached to the end of the lock connector 25, instillation (component transfusion, i.e. platelet transfusion in this case) into the vein of a patient is started. The flow rate of instillation is adjusted by the roller clamp 23.

When the blood preparation bag is emptied, the roller clamp 23 is closed and the clamp 20b is opened to introduce a rinse into the blood preparation bag. When 100 ml or so of the rinse is introduced, the clamp 20b is closed and the roller clamp 23 is again opened to resume the component transfusion. When the rinse in the blood preparation bag is exhausted, the rinse in the inlet-side tube 27 is recovered by opening an air vent 26, and the transfusion is finished.

Figure 8:
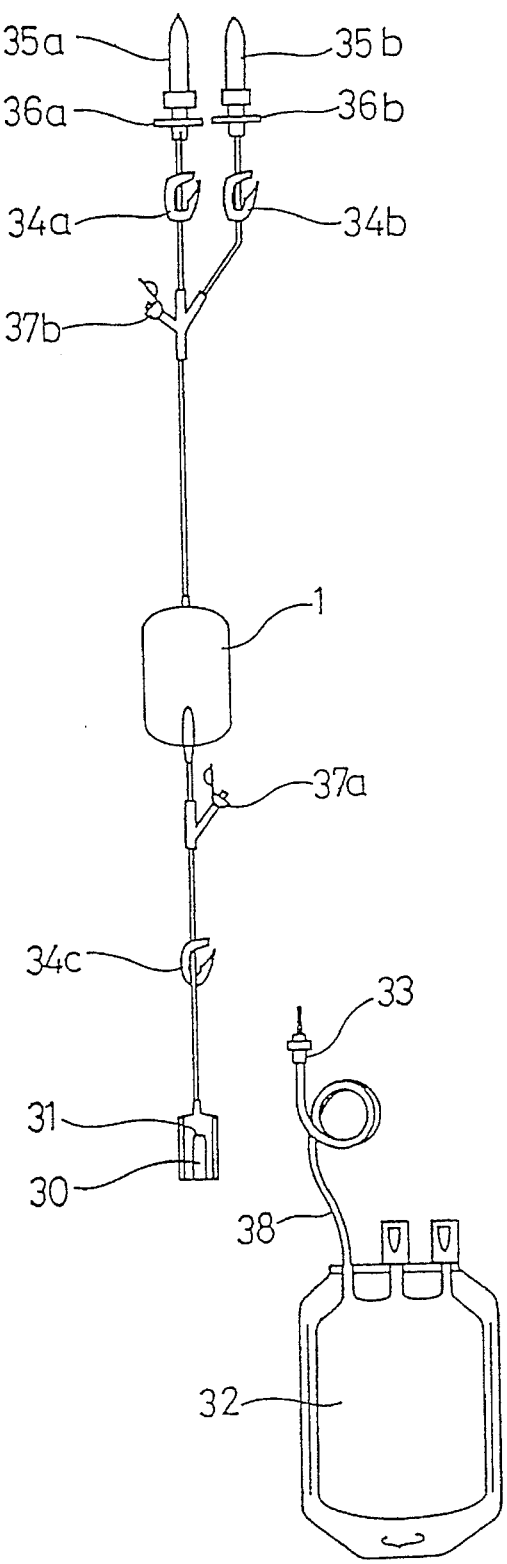
FIG. 8 is a schematic view showing another circuit including the leukocyte-separating filter according to the present invention.

Another example of usage of the leukocyte-separating filter 6 of the present invention will be explained below with reference to FIG. 8. The circuit of FIG. 8 uses the leukocyte-separating filter 6 of the present invention to remove leukocytes and recover platelets from a blood preparation not including red cells, such as a platelet concentrate. The separation of leukocytes by the circuit is substantially the same as that explained above, except for differences in that transfusion using the rinse is conducted and that the remover 1 does not include the air vent 12d whose function in the process stated above is performed by an air vent 37a. Incidentally, transfusion using a rinse may not be conducted in the circuit comprising leukocyte remover 1, and the leukocyte remover 1 may have the air vent 12d.

[4] Leukocyte/platelet remover

Figure 4:
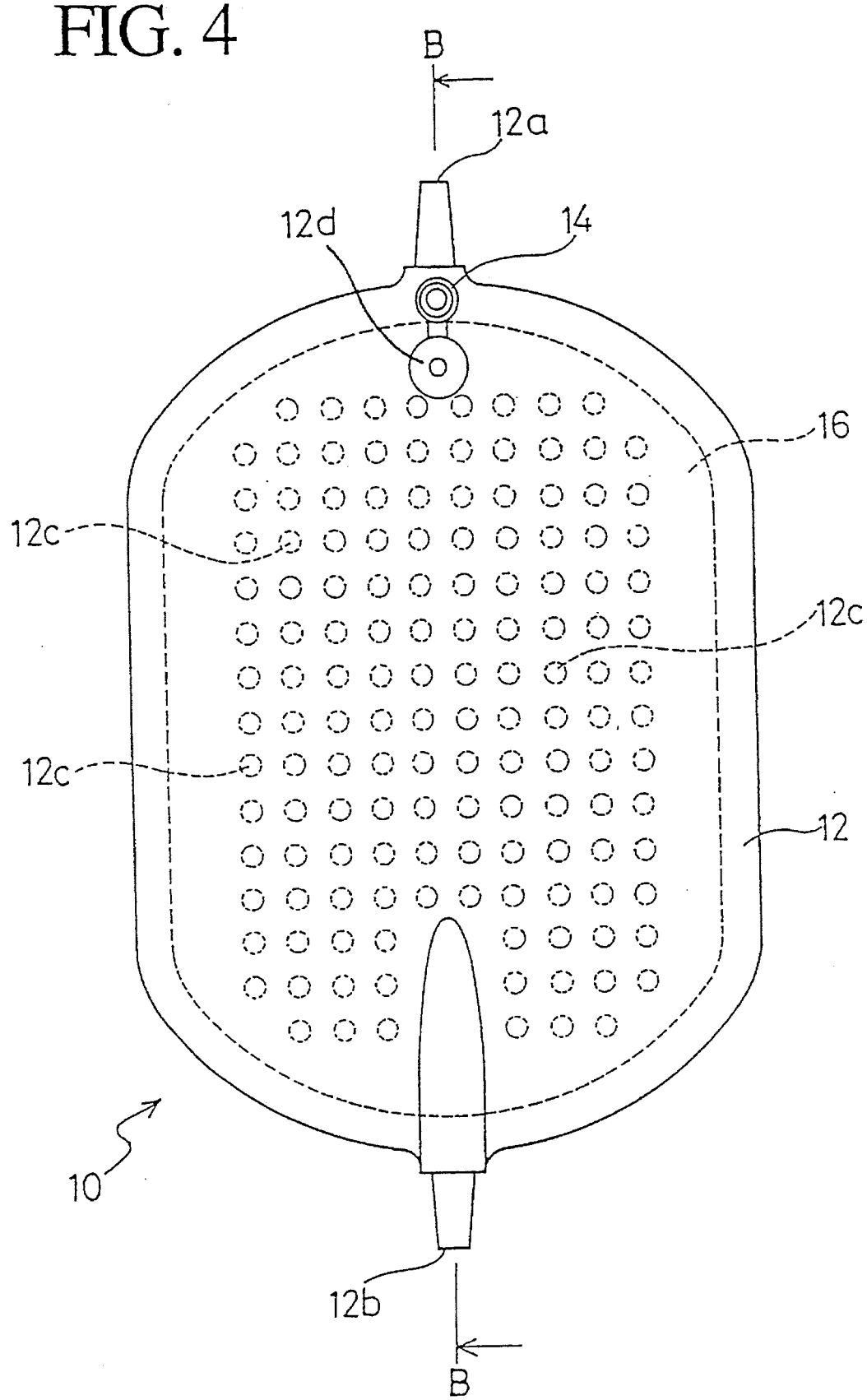
FIG. 4 is a front elevational view showing a leukocyte/platelet remover including a leukocyte/platelet-separating filter according to an embodiment of the present invention.
Figure 5:
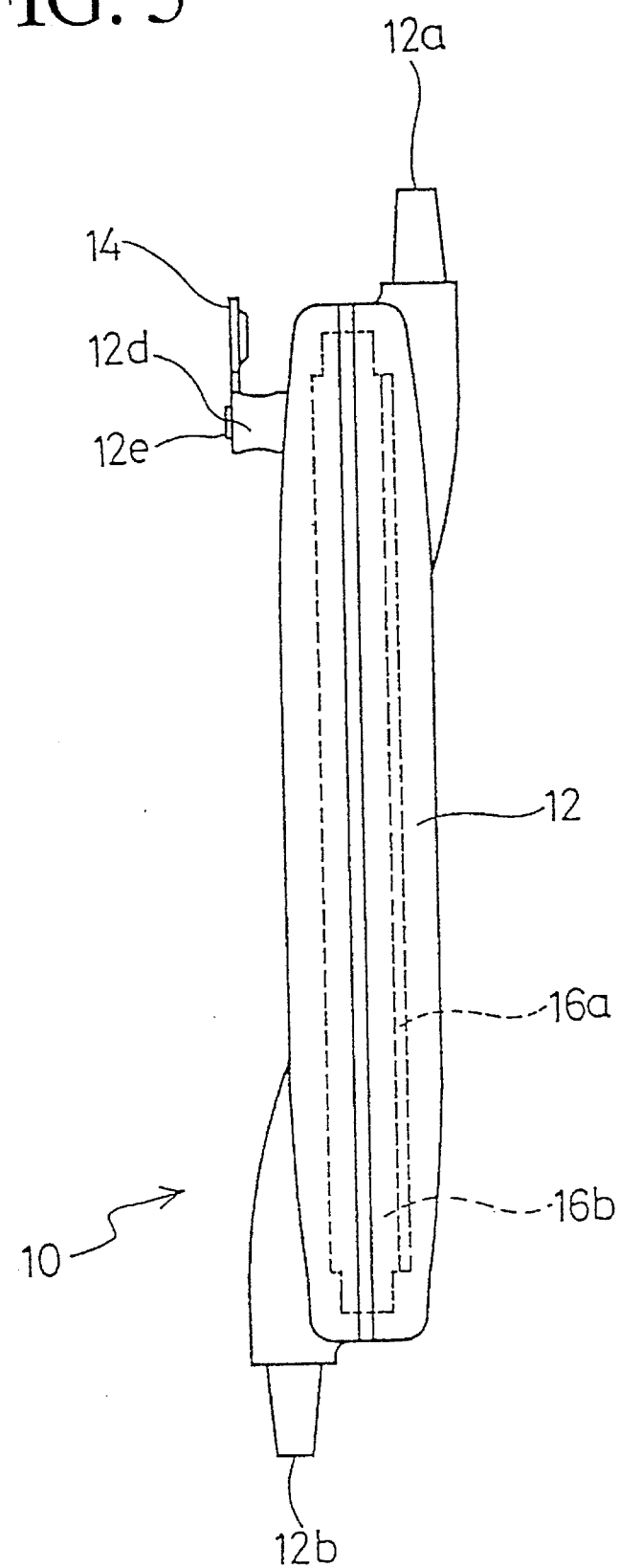
FIG. 5 is a right side elevational view of FIG. 4.
Figure 6:
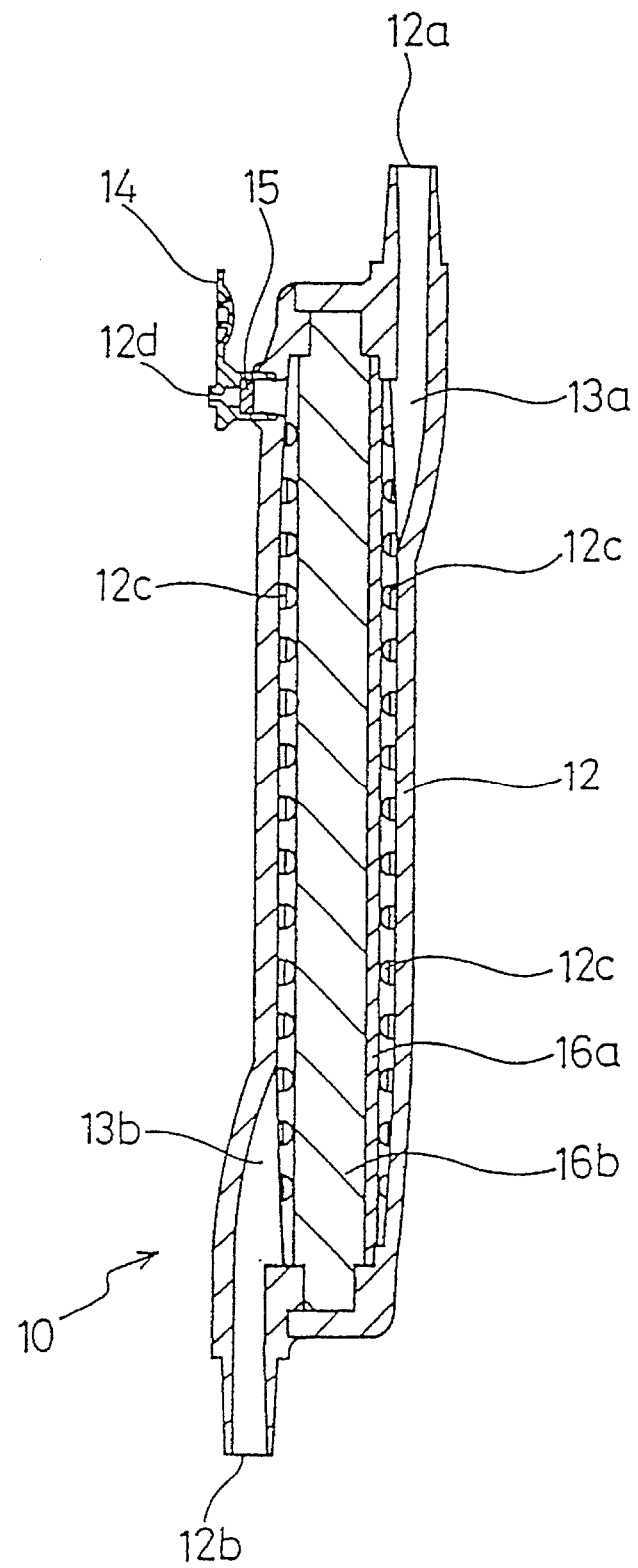
FIG. 6 is a cross-sectional view taken along the B—B line in FIG. 4.

A leukocyte/platelet-separating filter and a leukocyte/platelet remover comprising the leukocyte/platelet-separating filter according to the present invention will be explained below with reference to the drawings. FIG. 4 is a front elevation showing an example of the leukocyte/platelet remover comprising the leukocyte/platelet-separating filter according to the present invention. FIG. 5 is a right side elevational view of FIG. 4. FIG. 6 is a cross-sectional view taken along the B—B line in FIG. 4.

The leukocyte/platelet remover 10 comprising the leukocyte/platelet-separating filter 16 of the present invention includes a housing 12 having a blood inlet 12a and a blood outlet 12b, and the leukocyte/platelet-separating filter 16 disposed in the housing 2 such that it partitions the interior of the housing 12 into a blood inlet portion 13a and a blood outlet portion 13b. The leukocyte/platelet-separating filter 16 is composed of a pre-filter 16a for removing microaggregates and gels occurring in stored blood, and a platelet-adsorbing, three-dimensionally reticular, porous member with continuous open pores (main filter) 16b having a most frequent pore diameter of 1 μm to 5 μm and a ratio of a weight-average pore diameter to a number-average pore diameter in the range of 1.5 to 2.5. With this structure, the main filter 16 exhibits a good ability to capture both leukocytes and platelets.

The pre-filter 16a is preferably composed of non-woven fabrics in the form of a flat sheet each having a weight/area value of 30 $g/m^2$ to 80 $g/m^2$, an average fiber diameter of 10 μm to 20 μm and a thickness of about 0.3 mm to about 0.6 mm. Two to five such non-woven fabrics are preferably laminated. The main filter portion is preferably composed of a primary main filter portion having a wider pore diameter distribution and a secondary main filter portion having a narrower pore diameter distribution. The primary main filter portion is preferably composed of three-dimensionally reticular, porous members with continuous open pores each having a most frequent pore diameter of about 2 μm to about 3 μm, an average pore diameter ratio of 1.8 to 2.5 and a thickness of about 0.5 mm to about 2 mm. Two to five such porous members are preferably laminated. The secondary main filter portion is preferably composed of three-dimensionally reticular, porous members with continuous open pores each having a most frequent pore diameter of about 2 μm to about 3 μm, an average pore diameter ratio of 1.5 to 2.1 and a thickness of about 0.2 mm to about 2 mm. Two to five such porous members are preferably laminated. The porous members used for the secondary main filter portion may be the same as those used for the primary main filter portion.

In a preferred example, the pre-filter 16a is made by stacking three sheets of non-woven polyester fabrics each having an average fiber diameter of 12 μm and a bulk density of 0.1875 $g/cm^3$ or so to a thickness of about 0.1 mm. An upstream portion of the main filter 16b (the right side portion of the main filter 16b in FIG. 6) constitutes a primary main filter portion made by stacking on a 0.2-mm-thick sheet of non-woven polyester fabrics as a support member three surfactant-treated, porous polyurethane films each having a most frequent pore diameter of 1.0 μm to 3.0 μm, an average pore diameter ratio of 2.0 and a thickness of about 1.0 mm. A downstream portion of the main filter 16b (the left side portion of the main filter 16b in FIG. 6) constitutes a secondary main filter portion made by stacking three porous polyurethane films identical to those of the upstream portion but subjected to a cationic treatment and a surfactant treatment. Thus, the leukocyte/platelet-separating filter 16 of the present invention is preferably made by laminating a plurality of such porous members. The number of porous sheets stacked may be appropriately determined, considering such factors as removal rate, filtration time and likelihood of clogging.

Any surfactants may be used for a hydrophilic treatment, and suitable surfactants are, for example, deca-glycerol monolaurate, and polyether-type surfactants (for example, Pluronic surfactant). Instead of using a surfactant, the porous member may be subjected to a hydrophilic treatment (for example, plasma treatment).

The pre-filter 16a is used to remove microaggregates and gels originally contained in the blood or generated in the blood due to aggregation during storage. The porous member constituting the primary main filter portion disposed on the upstream side functions to remove leukocytes having larger diameters than its own pore diameters. Negative-charged platelets have smaller diameters than those of the porous member constituting the secondary main filter portion disposed on the downstream side. Nevertheless, since the porous member of the secondary main filter portion is positive-charged by a cationic treatment, platelets are electrically trapped by the porous member. Leukocytes passing through the primary main filter portion, although very few, are also removed by the secondary main filter portion. Also, red cells having larger diameters than the pore diameters of the porous members constituting the primary and secondary main filter portions can pass through the main filter 16b, because they are easily deformable.

Reasons why the porous member of the main filter 16b is combined with the non-woven fabrics are, among others, that the nonwoven fabrics having little anti-thrombogenic nature function to adsorb highly adherent platelets, that a step for stripping them in the sheet fabricating process can be omitted, that the porous member can be more easily mounted in the housing 2, and that the non-woven fabrics keep the porous member in a proper shape.

As shown in FIG. 6, the housing 12 of the leukocyte/platelet remover 10 has an air vent 12d near an upper portion. The air vent 12d facilitates the removal of an air in the course of priming the remover 10, the operation of starting or stopping filtration, the recovery of residual liquids in the remover, the removal of an air from the recovery bag, and so forth. Although the air vent 12d used in this embodiment can be opened and closed by a cap, it may be configured otherwise.

Figure 9:
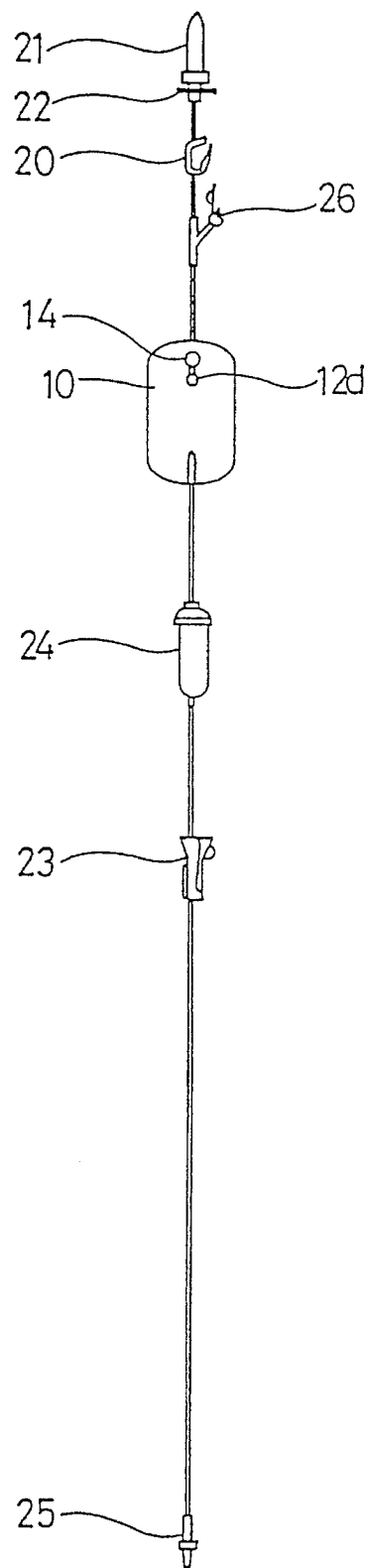
FIG. 9 is a schematic view showing a circuit including the leukocyte/platelet-separating filter according to the present invention.

An example of usage of the leukocyte/platelet-separating filter 16 according to the present invention will be explained below with reference to FIG. 9. The leukocyte/platelet remover 10 with the leukocyte/platelet-separating filter 16 according to the present invention is connected in a circuit as shown, for example, in FIG. 9. The circuit shown in FIG. 9 is for use in component transfusion of red cells to a patient while removing leukocytes and platelets from a whole blood or a blood preparation including red cells (for example, concentrated red cells) by using the leukocyte/platelet remover 10 including the leukocyte/platelet-separating filter 16 according to the present invention.

The process of separation of leukocytes and platelets by this circuit is the same as those stated above, except that transfusing operation by a rinse is not performed, and that the air vent 12d of the remover 10 is opened to transfuse red cells remaining in the tube on the outlet side to a patient after the blood preparation bag is emptied. The circuit comprising the leukocyte/platelet remover 10 may also be used for transfusing operation by a rinse, and the leukocyte/platelet remover 10 may not necessarily have the air vent 12d.

Figure 10:
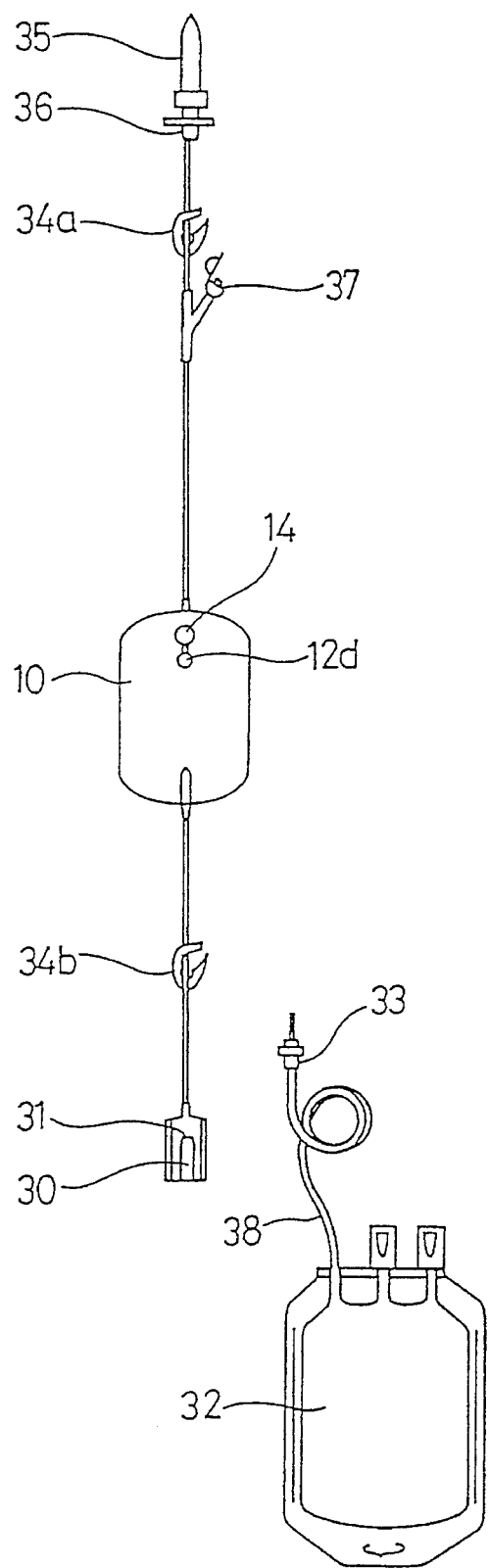
FIG. 10 is a schematic view showing another circuit including the leukocyte/platelet-separating filter according to the present invention.

Another example of usage of the leukocyte/platelet-separating filter 16 of the present invention will be explained with reference to FIG. 10. The circuit shown in FIG. 10 is intended to remove leukocytes and platelets and recover red cells from a whole blood or blood preparations including red cells by using the leukocyte/platelet remover 10 comprising the leukocyte/platelet-separating filter 16.

The process of separation of leukocytes by this circuit is conducted by opening a peel tab 30 and attaching a needle 33 of a recovery bag 32 to a vent 31, closing clamps 34a, 34b and a cap 14 of the air vent 12d, removing a protector 35, attaching a needle 36 to a blood preparation bag (not shown), and hanging it down from an irrigator (not shown).

The clamps 34a and the cap 14 of the air vent 12d are then opened for priming the remover 10. When the blood preparation reaches the air vent 12d, the air vent 12d is closed by the cap 14, and the clamp 34b is opened, thereby starting filtration.

When the blood preparation bag is emptied, a residual blood preparation on the inlet side is recovered by opening the air vent 37, and a residual blood preparation on the outlet side is recovered by opening the cap 14 of the air vent 12d. The residual blood preparation in the tube 38' on the outlet side is recovered in the bag 32 by squeezing the tube 38 with roller pincers. If there is a need for removal of an air from the recovery bag 32, the air can be expelled from the recovery bag 32 through the air vent 12d by moving the air toward the tube 38 and then pressing the recovery bag 32. Sealing the tube 38, the recovery bag 32 is detached from the circuit to finish the process of separating leukocytes and platelets.

The present invention will be explained in greater detail by way of Examples below without intention of limiting the present invention thereto.

EXAMPLE 1

Figure 11:
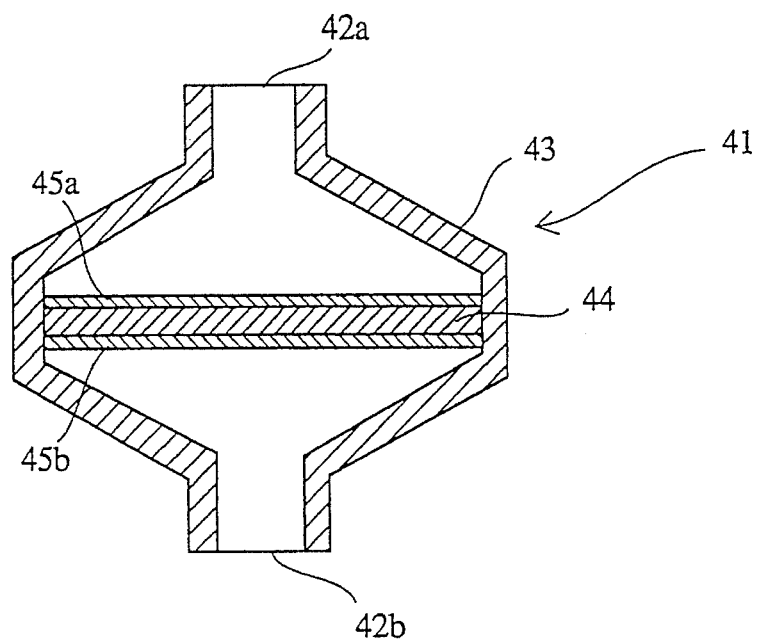
FIG. 11 is a cross-sectional view showing a leukocyte-separating filter used in Examples and Comparative Examples.
Figure 12:
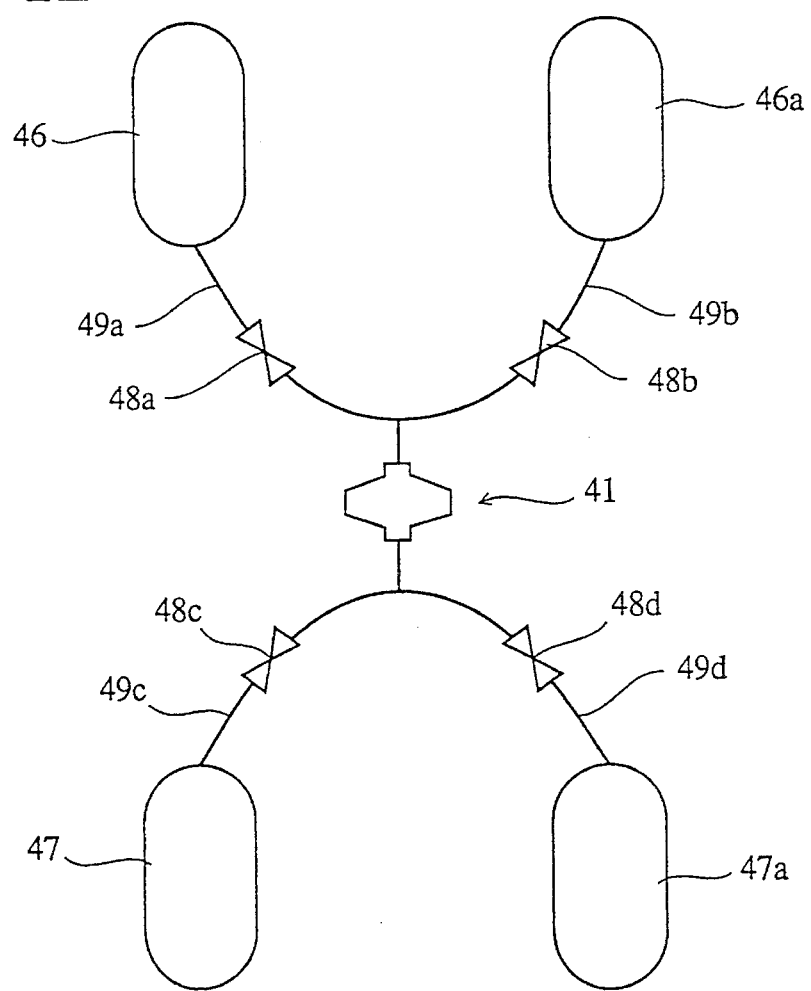
FIG. 12 is a schematic view showing an experimental circuit with a leukocyte-separating filter used in Examples and Comparative Examples.

A leukocyte-separating filter having the construction shown in FIG. 11 was made by using a porous polyvinyl formal sheet having a most frequent pore diameter of 2 μm to 3 μm, a dust permeability of 5, a porosity of 86%, a thickness of 1.3 mm and a filtration area of 50 cm$^2$, and the filter was mounted to the circuit of FIG. 12. In FIGS. 11 and 12, 41 denotes a leukocyte-separating filter, 42a a blood inlet, 42b a blood outlet, 43 a housing, 44 a porous polyvinyl formal member, 45a and 45b support members, 46 a blood bag, 46a a physiological saline solution bag, 47 a blood recovery bag, 47a a physiological saline solution recovery bag, 48a, 48b, 48c and 48d clamps, and 49a, 49b, 49c and 49d liquid tubes.

A unit of CPD-added concentrated red cells (CRC) obtained from 400 ml of the human blood was caused to flow through the separating filter gravitationally. The time required for the treatment was 6 minutes. The numbers of blood cells in CRC before and after the treatment were measured with an automatic blood cell counter (Sysmex NE-6000 produced by Toa Medical Electronics Co., Ltd.). The total numbers of respective blood cell components were measured on a liquid volume basis, and the red cell recovery rate and the leukocyte removal rate were determined. As a result, the red cell recovery rate was 98%, and the leukocyte removal rate was 90%.

EXAMPLE 2

A leukocyte-separating filter having the construction shown in FIG. 11 was made by using a porous polyurethane film having a most frequent pore size of 2 μm to 3 μm, a dust permeability of substantially zero, a porosity of 82%, a thickness of 1.0 mm and a filtration area of 50 cm², and the filter was mounted to the circuit of FIG. 12.

Ten units of CPD-added concentrated platelet concentrate (PC) obtained from 200 ml of the human blood were caused to flow through the separating filter gravitationally at an instillation speed of about 4 ml/minute. As a result, the drop speed did not decrease. The numbers of blood cells in PC before and after the treatment were measured with an automatic blood cell counter (Sysmex NE-6000 produced by Toa Medical Electronics Co., Ltd.) and a flow cytometer (Cyto-ACE 150 produced by Nippon Bunko K. K.). The total numbers of respective blood cell components were measured on a liquid volume basis, and the leukocyte removal rate and the platelet recovery rate were determined. The leukocyte removal rate was 99.9% and the platelet recovery rate was 95%.

EXAMPLE 3

Figure 13:
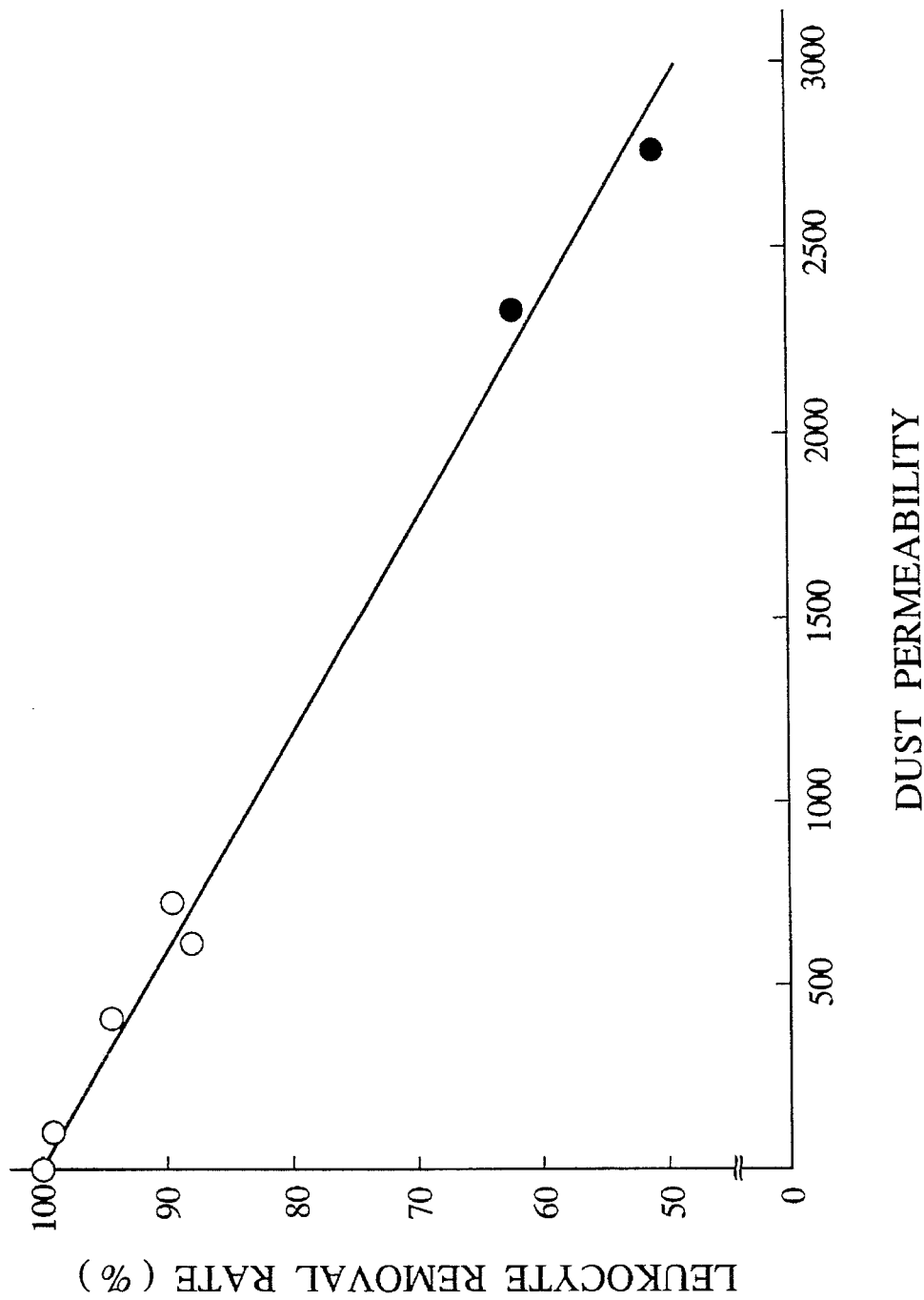
FIG. 13 is a graph showing the relation between a dust permeability and a leukocyte removal rate in leukocyte-separating filters.

Dust permeability was measured on porous polyvinyl formal members each having a most frequent pore diameter of 2 μm to 3 μm, a thickness of 1.3 mm and a porosity of 80% to 87% (A to F indicated by white circles in FIG. 13), and on porous polyvinyl formal members each having a most frequent pore diameter of 8 μm to 9 μm, a thickness of 1.3 mm and a porosity of 80% to 87% (G and H indicated by black circles in FIG. 13).

A leukocyte-separating filter having the construction shown in FIG. 11 (having a filtration area of 100 cm²) was composed of the above porous members, and it was mounted to the circuit of FIG. 12. One unit of CPD-added concentrated red cells (CRC) obtained from 400 ml of the human blood was caused to flow through the separating filter gravitationally. The numbers of blood cells in CRC before and after the treatment were measured with an automatic blood cell counter (Sysmex NE-6000 produced by Toa Medical Electronics Co., Ltd.). The total numbers of respective blood cell components were measured on a liquid volume basis, and the leukocyte removal rate was determined. The results are shown in Table 1 and FIG. 13.

TABLE 1

| | Filter | | | |
| --- | --- | --- | --- | --- |
| | A | B | C | D |
| Most Frequent Pore Diameter | 2–3 | 2–3 | 2–3 | 2–3 |
| Dust Permeability | 1 | 13 | 104 | 518 |
| Leukocyte Removal Rate | 99.7 | 99.3 | 98.9 | 94.5 |
| | E | F | G | H |
| Most Frequent Pore Diameter | 2–3 | 2–3 | 8–9 | 8–9 |
| Dust Permeability | 617 | 782 | 2459 | 2821 |
| Leukocyte Removal Rate | 88.1 | 89.6 | 61.8 | 52.0 |

The above results proved that filters composed of porous members whose most frequent pore diameters were in the range of 2 μm to 3 μm had small dust permeabilities and good leukocyte removal rates, while filters composed of porous members whose most frequent pore diameters were in the range of 8 μm to 9 μm provided large dust permeabilities and low leukocyte removal rates. Incidentally, the red cell recovery rate was 98% or more in all of the filters.

EXAMPLES 4–9, COMPARATIVE EXAMPLES 1–4

Leukocyte/platelet-separating filters having the construction shown in FIG. 4 were made by using porous polyvinyl formal members having a thickness of 1.3 mm, a filtration area of 50 cm², and most frequent pore diameters and average pore diameter ratios shown in Table 2. Since the porous polyvinyl formal members are hydrophilic and platelet-adsorbing, they were not subjected to any particular hydrophilic treatment and cationic treatment.

Every two of the porous members shown in Table 2 were stacked to make a leukocyte/platelet-separating filter, which was then assembled in a leukocyte/platelet remover as shown in FIG. 6. Each of such leukocyte/platelet removers was mounted to the circuit having the structure shown in FIG. 10. 0.5 units of CPD-added concentrated red cells (CRC) obtained from 400 ml of the human blood were caused to flow through the separating filter gravitationally.

The numbers of blood cells in CRC before and after the treatment, and the numbers of red cells and platelets after the treatment were measured with an automatic blood cell counter (Sysmex NE-6000 produced by Toa Medical Electronics Co., Ltd.). The total numbers of respective blood cell components were measured on a liquid volume basis, and the red cell recovery rates and the platelet removal rates were determined.

The numbers of leukocytes after the treatment were measured with a flow cytometer (Cyto-ACE 150 produced by Nippon Bunko K. K.) and a Nageotte hemocytometer. The total number of leukocytes was measured on a liquid volume basis, and the removal rate of leukocytes was determined. The results are shown in Table 3.

TABLE 2

| | Porous Member | |
| --- | --- | --- |
| No. | Most Frequent Pore Diameter (μm) | Average Pore Diameter Ratio |
| Example 4 | 1.0 | 2.0 |
| Example 5 | 2.0 | 1.9 |
| Example 6 | 3.5 | 1.8 |
| Example 7 | 4.0 | 1.7 |
| Example 8 | 4.5 | 2.5 |
| Example 9 | 5.0 | 2.0 |
| Com. Ex. 1 | 0.5 | 2.1 |
| Com. Ex. 2 | 2.0 | 1.4 |
| Com. Ex. 3 | 6.0 | 1.4 |
| Com. Ex. 4 | 6.0 | 2.0 |

TABLE 3

| | Separation Results | | | |
| --- | --- | --- | --- | --- |
| No. | Filtering Time (minute) | Leukocyte Removal Rate (%) | Red Cell Recovery Rate (%) | Platelet Removal Rate (%) |
| Example 4 | 14 | 99.9 | 97 | 92 |
| Example 5 | 12 | 99.9 | 97 | 92 |
| Example 6 | 11 | 99.9 | 97 | 91 |
| Example 7 | 10 | 99.9 | 97 | 91 |
| Example 8 | 8 | 99.5 | 98 | 90 |
| Example 9 | 10 | 99.7 | 98 | 90 |
| Com. Ex. 1 | 53 | 99.9 | 94 | 93 |
| Com. Ex. 2 | 47 | 99.9 | 92 | 92 |
| Com. Ex. 3 | 6 | 93.2 | 99 | 82 |
| Com. Ex. 4 | 5 | 91.0 | 99 | 77 |

Table 3 proves that the leukocyte/platelet-separating filters of Examples 4 to 9 composed of porous members having most frequent pore diameters in the range of 1 μm to 5 μm and average pore diameter ratios in the range of 1.5 to 2.5 exhibit good leukocyte removal rates in a practical period of time, and that their red cell recovery rates and platelet removal rates are better than those of Comparative Examples 1 to 4.

The same experiment was conducted with porous polyurethane members having a porosity of about 87%, a thickness of 1.3 mm, a filtration area of 50 cm², and most frequent pore diameters and average pore diameter ratios shown in Table 2. As a result, substantially the same results were obtained. Incidentally, a primary filter portion of the leukocyte/platelet-separating filter was produced by stacking three porous polyurethane members subjected to a hydrophilic treatment with glycerol monolaurate (decaglycerin monolaurate). A secondary filter portion of the leukocyte/platelet-separating filter was produced by using the same porous members as in the primary filter portion, by subjecting them to a plasma treatment, graft copolymerization with glycidyl methacrylate, fixing of a cationic agent (Cationon UK produced by Ipposha Oil & Fat Industries K. K.) and then a treatment with glycerol monolaurate, and by stacking three of them. The housing used was configured as shown in FIGS. 4 to 6. The housing contained the separating filter to form the leukocyte/platelet remover as shown in FIG. 6.

EXAMPLES 10–13, COMPARATIVE EXAMPLES 5–7

Figure 14:
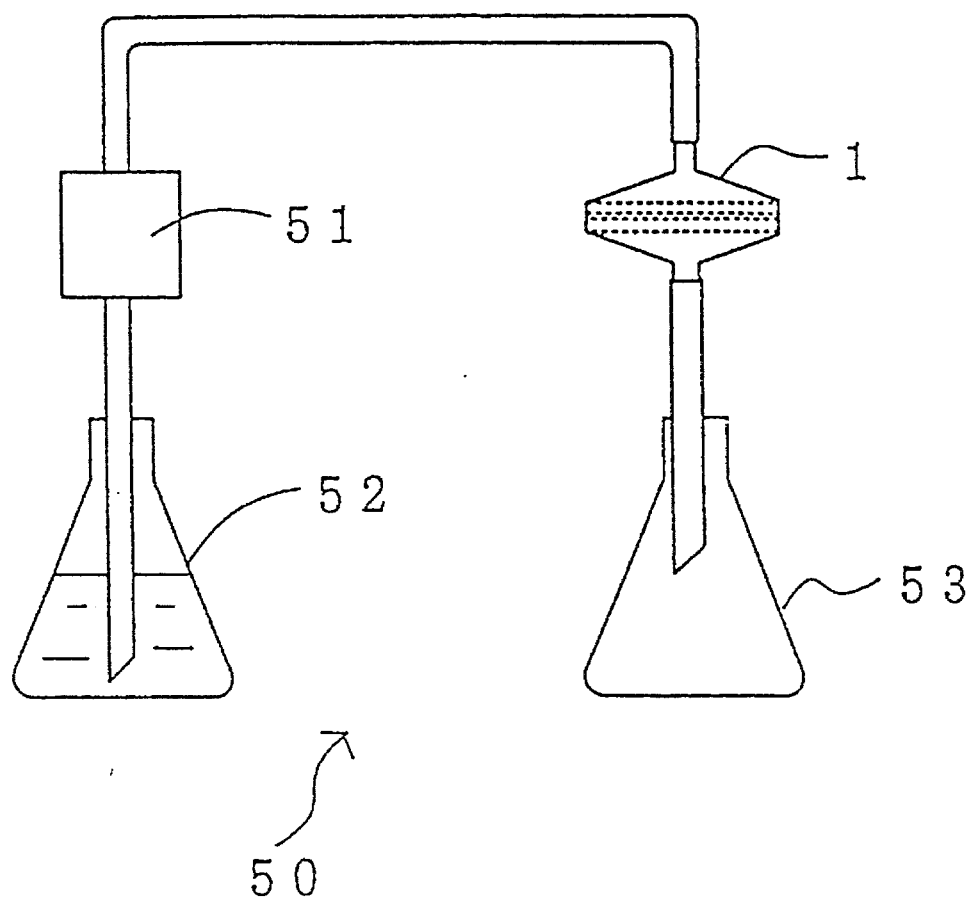
FIG. 14 is a schematic view showing an experimental circuit with a leukocyte-separating filter used in Examples and Comparative Examples.

A leukocyte/platelet-separating filter shown in FIG. 14 was made by using porous polyurethane members having a thickness of 0.6 mm, a filtration area of 3 cm², a porosity of about 87%, and most frequent pore diameters and average pore diameter ratios shown in Table 4. The filter included a pre-filter portion made by stacking two such porous members shown in Table 4 subjected to a hydrophilic treatment with glycerol monolaurate, and a main filter portion made by stacking four such porous members treated by glycerol monolaurate like those of the pre-filter portion. The housing used was configured as shown in FIG. 14, and contained the above separating filter to form a leukocyte remover.

The leukocyte-separating filters of Examples 10 to 13 and Comparative Examples 5 to 7 were incorporated into circuits having the construction shown in FIG. 14 to form experimental circuits. Lymphocyte-containing, platelet-rich plasma (PRP) (platelets: 3.5×10⁵/μl–5.5×10⁵/μl, and leukocytes: 3.5×10³/μl–4.5× 10³/μl) was prepared by adding self-lymphocytes separated by a density-gradient centrifugal separation method to a platelet-rich plasma (PRP) collected from CPD-added fresh blood of healthy humans. The experiment was conducted by passing the lymphocyte-containing PRP through the experimental circuits shown in FIG. 14 at a flow rate of 1 ml/minute.cm².

The numbers of platelets in PRP before and after the treatment and the numbers of leukocytes in PRP before the treatment were measured with an automatic blood cell counter (Sysmex NE-6000 produced by Toa Medical Electronics Co., Ltd.), and the number of leukocytes after the treatment was measured with a flow cytometer (Cyto-ACE 150 produced by Nippon Bunko K. K.) and a Nageotte hemocytometer. The total numbers of respective blood cell components were measured on a liquid volumes basis, and the leukocyte removal rates and the platelet recovery rates were calculated therefrom. The results are shown in Table 5.

TABLE 4

| | Porous Member | | | |
|---|---|---|---|---|
| | Pre-filter Portion | | Main Filter Portion | |
| No. | Most Frequent Pore Diameter | Average Pore Diameter Ratio | Most Frequent Pore Diameter | Average Pore Diameter Ratio |
| Example 10 | 3.5 μm | 1.8 | 1.0 μm | 2.0 |
| Example 11 | 3.5 μm | 1.8 | 2.0 μm | 1.9 |
| Example 12 | 4.0 μm | 1.7 | 2.0 μm | 1.9 |
| Example 13 | 4.5 μm | 2.5 | 1.0 μm | 2.0 |
| Com. Ex. 5 | 5.0 μm | 2.0 | 1.0 μm | 2.0 |
| Com. Ex. 6 | 6.0 μm | 2.0 | 0.5 μm | 2.1 |
| Com. Ex. 7 | 6.0 μm | 2.0 | 2.0 μm | 1.4 |

TABLE 5

| | Separation Results | |
|---|---|---|
| No. | Leukocyte Removal Rate (%) | Platelet Recovery Rate (%) |
| Example 10 | 99.99 | 91 |
| Example 11 | 99.99 | 93 |
| Example 12 | 99.99 | 92 |
| Example 13 | 99.99 | 91 |
| Com. Ex. 5 | 99.75 | 91 |
| Com. Ex. 6 | —* | —* |
| Com. Ex. 7 | 99.23 | 94 |

Note: *No flow by clogging.

Table 5 proves that the leukocyte filters of Examples 10 to 13 composed of porous members having most frequent pore diameters in the range of 1 μm to 5 μm and average pore diameter ratios in the range of 1.5 to 2.5 exhibited better leukocyte removal rates and platelet removal rates than those of Comparative Examples 5 to 7.

As explained above, since the leukocyte-separating filters of the present invention are composed of three-dimensionally reticular, porous member with continuous open pores having most frequent pore diameters ranging from 1 μm to 5 μm and a permeability of 200 or less for dust particles having diameters not less than 0.3 μm in the air, they exhibit high and stable abilities to capture leukocytes. Thus, leukocytes contained in the blood are efficiently and quickly captured when passing through complicated flow paths of continuous open pores in the matrix of the porous member. By meeting the requirement that the ratio of a weight-average pore diameter to a number-average pore diameter is in the range of 1.5 to 2.5, the leukocyte removal rate is further improved. Since the flow path of the filter is defined by the three-dimensionally reticular, continuous texture of a porous member (continuous open pores defined by the matrix of the porous member), the filter is stable and uniform in performance. The filter also suffers from substantially no outflow of foreign matters from the porous members and channeling of the flow paths during operation. Moreover, since the flow paths of the filter are formed at the time of production of the porous member, the filter can very easily be fabricated.

What is claimed is:

1. A leukocyte-separating filter composed of a plurality of three-dimensionally reticular, porous members with continuous open pores having a most frequent pore diameter in the range of 1 μm to 5 μm and a ratio of a weight-average pore diameter to a number-average pore diameter in the range of 1.5 to 2.5, one or more of said porous members located on the upstream side having a ratio of the weight-average pore diameter to the number-average pore diameter larger than that of the remaining porous members located on the downstream side.

2. The leukocyte-separating filter according to claim 1, wherein said porous member does not adsorb platelets.

3. The leukocyte-separating filter according to claim 1, wherein at least one of said three-dimensionally reticular, porous members is made of a platelet-adsorbing material.

* * * * *

UNITED STATES PATENT AND TRADEMARK OFFICE
CERTIFICATE OF CORRECTION

PATENT NO. : 5,476,587
DATED : December 19, 1995
INVENTOR(S) : Hitoshi KUROKI et al It is certified that error appears in the above-indentified patent and that said Letters Patent is hereby corrected as shown below:

In Column 6, line 19, delete "fiat" and insert -- flat --.

In Column 6, line 26, delete "fiat" and insert -- flat --.

In Column 8, line 57, delete "min" and insert -- mm --.

Signed and Sealed this

Twenty-third Day of April, 1996

*Attest:*

BRUCE LEHMAN

*Attesting Officer*   Commissioner of Patents and Trademarks